(12) United States Patent
Denison et al.

(10) Patent No.: US 7,572,272 B2
(45) Date of Patent: *Aug. 11, 2009

(54) EMBOLIC FILTERING DEVICES FOR BIFURCATED VESSELS

(75) Inventors: Andy E. Denison, Temecula, CA (US); William J. Boyle, Fallbrook, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 11/108,309

(22) Filed: Apr. 18, 2005

(65) Prior Publication Data

US 2005/0182441 A1    Aug. 18, 2005

Related U.S. Application Data

(63) Continuation of application No. 10/180,287, filed on Jun. 26, 2002, now Pat. No. 6,887,258.

(51) Int. Cl.
*A61M 29/00* (2006.01)
*A61B 17/22* (2006.01)
*A61D 1/02* (2006.01)
*A61F 2/06* (2006.01)

(52) U.S. Cl. .................. 606/200; 606/127; 606/159; 623/1.35

(58) Field of Classification Search .......... 606/110, 606/113, 114, 127, 128, 151, 159, 200, 213
See application file for complete search history.

(56) References Cited

U.S. PATENT DOCUMENTS 3,952,747 A    4/1976    Kimmell, Jr.

4,425,908 A    1/1984    Simon (Continued)

FOREIGN PATENT DOCUMENTS

EP    0427429 A3    9/1991

(Continued)

OTHER PUBLICATIONS

Dilitation of the Carotid Artery By A Temporary Carotid Filter By A. Beck, St. Milic, A.M. Spagnoli, November-December Issue of OPLITAI, An International Journal on Military Medicine and Health Emergencies, pp. 67-74.

*Primary Examiner*—Todd E Manahan
*Assistant Examiner*—Diane Yabut
(74) *Attorney, Agent, or Firm*—Fulwider Patton LLP

(57) ABSTRACT

An embolic filtering device for use in a bifurcated vessel includes delivery device having a first guide wire and a second guide wire. The second guide wire diverges from the distal-end region of the first guide wire. The filter device also includes a filter support having a first deployment member and a second deployment member. These deployment members can be formed as a first loop and a second loop. A bifurcated filter element is coupled to the filter support. The distal-end region of the first guide wire extends through a first leg of the filter element and the second guide wire extends through a second leg of the filter element. During use, the first leg of the filter element is deployed within a first branch of the bifurcated vessel and the second leg of the filter element is deployed within a second branch of the bifurcated vessel.

14 Claims, 4 Drawing Sheets

U.S. PATENT DOCUMENTS

| | | |
|---|---|---|
| 4,494,531 A | 1/1985 | Gianturco |
| 4,552,554 A * | 11/1985 | Gould et al. ................ 604/506 |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,980 A | 3/1997 | Chauhan |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |

| | | |
|---|---|---|
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,786 B2 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |

| | | | | | |
|---|---|---|---|---|---|
| 6,652,557 B1 | 11/2003 | MacDonald | 6,932,830 B2 | 8/2005 | Ungs |
| 6,656,202 B2 | 12/2003 | Papp et al. | 6,932,831 B2 | 8/2005 | Forber |
| 6,656,203 B2 | 12/2003 | Roth et al. | 6,936,058 B2 | 8/2005 | Forde et al. |
| 6,656,204 B2 | 12/2003 | Ambrisco et al. | 6,936,059 B2 | 8/2005 | Belef |
| 6,656,351 B2 | 12/2003 | Boyle | 6,939,361 B1 | 9/2005 | Kleshinski |
| 6,660,021 B1 | 12/2003 | Palmer et al. | 6,939,362 B2 | 9/2005 | Boyle et al. |
| 6,663,650 B2 | 12/2003 | Sepetka et al. | 6,942,673 B2 | 9/2005 | Bates et al. |
| 6,663,651 B2 | 12/2003 | Krolik et al. | 6,949,103 B2 | 9/2005 | Mazzocchi et al. |
| 6,663,652 B2 | 12/2003 | Daniel et al. | 6,951,570 B2 | 10/2005 | Linder et al. |
| 6,673,090 B2 | 1/2004 | Root et al. | 6,953,471 B1 | 10/2005 | Lilly et al. |
| 6,676,666 B2 | 1/2004 | Vrba et al. | 6,953,472 B2 | 10/2005 | Palmer et al. |
| 6,676,682 B1 | 1/2004 | Tsugita et al. | 6,958,074 B2 | 10/2005 | Russell |
| 6,676,683 B1 | 1/2004 | Addis | 6,960,370 B2 | 11/2005 | Monni et al. |
| 6,679,902 B1 | 1/2004 | Boyle et al. | 6,962,598 B2 | 11/2005 | Linder et al. |
| 6,679,903 B2 | 1/2004 | Kurz | 6,964,670 B1 | 11/2005 | Shah |
| 6,682,546 B1 | 1/2004 | Amplatz | 6,964,672 B2 | 11/2005 | Brady |
| 6,685,722 B1 | 2/2004 | Rosenbluth et al. | 6,964,673 B2 | 11/2005 | Tsugita et al. |
| 6,689,151 B2 | 2/2004 | Becker et al. | 6,969,395 B2 | 11/2005 | Eskuri |
| 6,692,513 B2 | 2/2004 | Streeter et al. | 6,969,396 B2 | 11/2005 | Krolik et al. |
| 6,695,813 B1 | 2/2004 | Boyle et al. | 6,969,402 B2 | 11/2005 | Bales et al. |
| 6,695,858 B1 | 2/2004 | Dubrul et al. | 6,970,730 B2 | 11/2005 | Fuimaono et al. |
| 6,695,864 B2 | 2/2004 | Macoviak et al. | 6,972,025 B2 | 12/2005 | WasDyke |
| 6,696,666 B2 | 2/2004 | Merdan et al. | 6,973,340 B2 | 12/2005 | Fuimaono et al. |
| 6,699,260 B2 | 3/2004 | Dubrul et al. | 6,974,468 B2 | 12/2005 | DoBrava et al. |
| 6,702,834 B1 | 3/2004 | Boyle et al. | 6,974,469 B2 | 12/2005 | Broome et al. |
| 6,706,055 B2 | 3/2004 | Douk et al. | 6,979,343 B2 | 12/2005 | Russo |
| 6,712,834 B2 | 3/2004 | Yassour et al. | 6,979,344 B2 | 12/2005 | Jones et al. |
| 6,712,835 B2 | 3/2004 | Mazzocchi et al. | 6,986,778 B2 | 1/2006 | Zadno-Azizi |
| 6,716,231 B1 | 4/2004 | Rafiee et al. | 6,989,021 B2 | 1/2006 | Bosma et al. |
| 6,723,085 B2 | 4/2004 | Jang et al. | 6,989,027 B2 | 1/2006 | Allen et al. |
| 6,726,701 B2 | 4/2004 | Gilson | 6,991,641 B2 | 1/2006 | Diaz et al. |
| 6,726,702 B2 | 4/2004 | Khosravi | 6,991,642 B2 | 1/2006 | Peterson |
| 6,726,703 B2 | 4/2004 | Broome et al. | 9,989,019 | 1/2006 | Mazzocchi |
| 6,740,061 B1 | 5/2004 | Oslund et al. | RE38,972 E | 2/2006 | Purdy |
| 6,743,247 B1 | 6/2004 | Levinson et al. | 6,994,718 B2 | 2/2006 | Groothuis et al. |
| 6,746,469 B2 | 6/2004 | Mouw | 6,997,938 B2 | 2/2006 | Wang et al. |
| 6,752,819 B1 | 6/2004 | Brady et al. | 6,997,939 B2 | 2/2006 | Linder et al. |
| 6,755,846 B1 | 6/2004 | Yadav | 7,001,406 B2 | 2/2006 | Eskuri et al. |
| 6,758,855 B2 | 7/2004 | Fulton, III et al. | 7,001,407 B2 | 2/2006 | Hansen et al. |
| 6,761,727 B1 | 7/2004 | Ladd | 7,004,954 B1 | 2/2006 | Voss et al. |
| 6,773,448 B2 | 8/2004 | Kusleika et al. | 7,004,955 B2 | 2/2006 | Shen et al. |
| 6,790,219 B1 | 9/2004 | Murphy | 7,004,956 B2 | 2/2006 | Palmer et al. |
| 6,793,666 B2 | 9/2004 | Hansen et al. | 7,004,964 B2 | 2/2006 | Thompson et al. |
| 6,793,668 B1 | 9/2004 | Fisher | 7,011,671 B2 | 3/2006 | Welch |
| 6,800,080 B1 | 10/2004 | Bates | 7,011,672 B2 | 3/2006 | Barbut et al. |
| 6,814,739 B2 | 11/2004 | Secrest et al. | 7,014,647 B2 | 3/2006 | Brady et al. |
| 6,818,006 B2 | 11/2004 | Douk et al. | 7,018,372 B2 | 3/2006 | Casey |
| 6,837,898 B2 | 1/2005 | Boyle | 7,018,385 B2 | 3/2006 | Bates et al. |
| 6,840,950 B2 | 1/2005 | Stanford et al. | 7,018,393 B1 | 3/2006 | Boyle et al. |
| 6,843,798 B2 | 1/2005 | Kusleika et al. | 7,029,440 B2 | 4/2006 | Broome et al. |
| 6,846,316 B2 | 1/2005 | Abrams | 7,033,375 B2 | 4/2006 | Mazzocchi et al. |
| 6,846,317 B1 | 1/2005 | Nigon | 7,037,320 B2 | 5/2006 | Brady et al. |
| 6,863,696 B2 | 3/2005 | Kantsevitcha et al. | 7,041,116 B2 | 5/2006 | Goto et al. |
| 6,866,677 B2 | 3/2005 | Douk et al. | 7,044,958 B2 | 5/2006 | Douk et al. |
| 6,872,216 B2 | 3/2005 | Daniel et al. | 7,048,752 B2 | 5/2006 | Mazzocchi |
| 6,878,151 B2 | 4/2005 | Carrison et al. | 7,048,758 B2 | 5/2006 | Boyle et al. |
| 6,878,153 B2 | 4/2005 | Linder et al. | 7,056,328 B2 | 6/2006 | Arnott |
| 6,887,256 B2 | 5/2005 | Gilson et al. | 7,060,082 B2 | 6/2006 | Goll et al. |
| 6,887,257 B2 | 5/2005 | Salahieh et al. | 7,077,854 B2 | 7/2006 | Khosravi |
| 6,887,258 B2 * | 5/2005 | Denison et al. ............. 606/200 | 7,094,243 B2 | 8/2006 | Mulholland |
| 6,888,098 B1 | 5/2005 | Merdan et al. | 7,094,249 B1 | 8/2006 | Broome et al. |
| 6,890,340 B2 | 5/2005 | Duane | 7,097,440 B2 | 8/2006 | Boyle et al. |
| 6,890,341 B2 | 5/2005 | Dieck et al. | 7,097,651 B2 | 8/2006 | Harrison et al. |
| 6,893,450 B2 | 5/2005 | Foster | 7,101,379 B2 | 9/2006 | Gregory, Jr et al. |
| 6,893,451 B2 | 5/2005 | Cano et al. | 7,101,380 B2 | 9/2006 | Khachin et al. |
| 6,896,690 B1 | 5/2005 | Lambrecht et al. | 7,108,707 B2 | 9/2006 | Huter et al. |
| 6,896,691 B2 | 5/2005 | Boylan | 7,241,304 B2 * | 7/2007 | Boyle et al. ................ 606/200 |
| 6,902,540 B2 | 6/2005 | Dorros et al. | 2002/0091408 A1 | 7/2002 | Sutton et al. |
| 6,908,474 B2 | 6/2005 | Hogenkijk et al. | 2002/0091409 A1 | 7/2002 | Sutton et al. |
| 6,911,036 B2 | 6/2005 | Douk et al. | 2002/0095141 A1 | 7/2002 | Belef et al. |
| 6,913,612 B2 | 7/2005 | Palmer et al. | 2002/0099407 A1 | 7/2002 | Becker et al. |
| 6,918,921 B2 | 7/2005 | Brady et al. | 2002/0103501 A1 | 8/2002 | Diaz et al. |
| 6,929,652 B1 | 8/2005 | Andrews | 2002/0107541 A1 | 8/2002 | Vale et al. |

| | | | | | |
|---|---|---|---|---|---|
| 2002/0111648 A1 | 8/2002 | Kusleika et al. | 2003/0130682 A1 | 7/2003 | Broome et al. |
| 2002/0111659 A1 | 8/2002 | Russo et al. | 2003/0130684 A1 | 7/2003 | Brady et al. |
| 2002/0115942 A1 | 8/2002 | Stanford et al. | 2003/0130685 A1 | 7/2003 | Daniel et al. |
| 2002/0120286 A1 | 8/2002 | Dobrava et al. | 2003/0130686 A1 | 7/2003 | Daniel et al. |
| 2002/0120287 A1 | 8/2002 | Huter | 2003/0130687 A1 | 7/2003 | Daniel et al. |
| 2002/0121472 A1 | 9/2002 | Garner et al. | 2003/0130688 A1 | 7/2003 | Daniel et al. |
| 2002/0123720 A1 | 9/2002 | Kusleika et al. | 2003/0135162 A1 | 7/2003 | Deyette, Jr. et al. |
| 2002/0123755 A1 | 9/2002 | Lowe et al. | 2003/0135232 A1 | 7/2003 | Douk et al. |
| 2002/0128679 A1 | 9/2002 | Turovskiy et al. | 2003/0139764 A1 | 7/2003 | Levinson et al. |
| 2002/0128680 A1 | 9/2002 | Pavlovic | 2003/0144685 A1 | 7/2003 | Boyle et al. |
| 2002/0128681 A1 | 9/2002 | Broome et al. | 2003/0144689 A1 | 7/2003 | Brady et al. |
| 2002/0133092 A1 | 9/2002 | Oslund et al. | 2003/0150821 A1 | 8/2003 | Bates et al. |
| 2002/0138094 A1 | 9/2002 | Borillo et al. | 2003/0153935 A1 | 8/2003 | Mialhe |
| 2002/0138095 A1 | 9/2002 | Mazzocchi et al. | 2003/0153942 A1 | 8/2003 | Wang et al. |
| 2002/0143360 A1 | 10/2002 | Douk et al. | 2003/0153943 A1 | 8/2003 | Michael et al. |
| 2002/0143361 A1 | 10/2002 | Douk et al. | 2003/0158574 A1 | 8/2003 | Esch et al. |
| 2002/0151927 A1 | 10/2002 | Douk et al. | 2003/0163064 A1 | 9/2003 | Kusleika et al. |
| 2002/0156456 A1 | 10/2002 | Fisher | 2003/0171770 A1 | 9/2003 | Anderson et al. |
| 2002/0156457 A1 | 10/2002 | Fisher | 2003/0171771 A1 | 9/2003 | Shimon |
| 2002/0161390 A1 | 10/2002 | Mouw | 2003/0171803 A1 | 9/2003 | Berrada et al. |
| 2002/0161392 A1 | 10/2002 | Dubrul | 2003/0176884 A1 | 9/2003 | Broome et al. |
| 2002/0161393 A1 | 10/2002 | Demond et al. | 2003/0176885 A1 | 9/2003 | Wholey et al. |
| 2002/0161395 A1 | 10/2002 | Douk et al. | 2003/0176886 A1 | 9/2003 | Sutton et al. |
| 2002/0165576 A1 | 11/2002 | Boyle et al. | 2003/0176889 A1 | 9/2003 | Boyle et al. |
| 2002/0169414 A1 | 11/2002 | Kletschka | 2003/0181942 A1 | 9/2003 | Daniel et al. |
| 2002/0169458 A1 | 11/2002 | Connors, III | 2003/0186102 A1 | 10/2003 | Keegan et al. |
| 2002/0169472 A1 | 11/2002 | Douk et al. | 2003/0187474 A1 | 10/2003 | Keegan et al. |
| 2002/0169474 A1 | 11/2002 | Kusleika et al. | 2003/0187475 A1 | 10/2003 | Tsugita et al. |
| 2002/0173815 A1 | 11/2002 | Hogendijk et al. | 2003/0187495 A1 | 10/2003 | Cully et al. |
| 2002/0173817 A1 | 11/2002 | Kletschka et al. | 2003/0191493 A1 | 10/2003 | Epstein et al. |
| 2002/0188313 A1 | 12/2002 | Johnson et al. | 2003/0195554 A1 | 10/2003 | Shen et al. |
| 2002/0188314 A1 | 12/2002 | Anderson et al. | 2003/0195555 A1 | 10/2003 | Khairkhahan et al. |
| 2002/0193825 A1 | 12/2002 | McGuckin et al. | 2003/0195556 A1 | 10/2003 | Stack et al. |
| 2002/0193826 A1 | 12/2002 | McGuckin et al. | 2003/0199819 A1 | 10/2003 | Beck |
| 2002/0193827 A1 | 12/2002 | McGuckin et al. | 2003/0199921 A1 | 10/2003 | Palmer et al. |
| 2002/0193828 A1 | 12/2002 | Griffin et al. | 2003/0204168 A1 | 10/2003 | Bosme et al. |
| 2003/0004536 A1 | 1/2003 | Boylan et al. | 2003/0204202 A1 | 10/2003 | Palmer et al. |
| 2003/0004537 A1 | 1/2003 | Boyle et al. | 2003/0208222 A1 | 11/2003 | Zadno-Azizi |
| 2003/0004539 A1 | 1/2003 | Linder et al. | 2003/0208224 A1 | 11/2003 | Broome |
| 2003/0004540 A1 | 1/2003 | Linder et al. | 2003/0208225 A1 | 11/2003 | Goll et al. |
| 2003/0004541 A1 | 1/2003 | Linder et al. | 2003/0208226 A1 | 11/2003 | Bruckheimer et al. |
| 2003/0009188 A1 | 1/2003 | Linder et al. | 2003/0208227 A1 | 11/2003 | Thomas |
| 2003/0009189 A1 | 1/2003 | Gilson et al. | 2003/0208228 A1 | 11/2003 | Gilson et al. |
| 2003/0015206 A1 | 1/2003 | Roth et al. | 2003/0208229 A1 | 11/2003 | Kletschka |
| 2003/0018354 A1 | 1/2003 | Roth et al. | 2003/0212361 A1 | 11/2003 | Boyle et al. |
| 2003/0023265 A1 | 1/2003 | Forber | 2003/0212429 A1 | 11/2003 | Keegan et al. |
| 2003/0028238 A1 | 2/2003 | Burkett et al. | 2003/0212431 A1 | 11/2003 | Brady et al. |
| 2003/0032941 A1 | 2/2003 | Boyle et al. | 2003/0212434 A1 | 11/2003 | Thielen |
| 2003/0032977 A1 | 2/2003 | Brady et al. | 2003/0216774 A1 | 11/2003 | Larson |
| 2003/0040772 A1 | 2/2003 | Hyodoh et al. | 2003/0220665 A1 | 11/2003 | Eskuri et al. |
| 2003/0042186 A1 | 3/2003 | Boyle et al. | 2003/0225418 A1 | 12/2003 | Eskuri et al. |
| 2003/0045898 A1 | 3/2003 | Harrison et al. | 2003/0225435 A1 | 12/2003 | Huter et al. |
| 2003/0057156 A1 | 3/2003 | Peterson et al. | 2003/0229295 A1 | 12/2003 | Houde et al. |
| 2003/0060782 A1 | 3/2003 | Bose et al. | 2003/0229374 A1 | 12/2003 | Brady et al. |
| 2003/0060843 A1 | 3/2003 | Boucher | 2003/0233117 A1 | 12/2003 | Adams et al. |
| 2003/0060844 A1 | 3/2003 | Borillo et al. | 2003/0236545 A1 | 12/2003 | Gilson |
| 2003/0065354 A1 | 4/2003 | Boyle et al. | 2004/0002730 A1 | 1/2004 | Denison et al. |
| 2003/0069596 A1 | 4/2003 | Eskuri | 2004/0006361 A1 | 1/2004 | Boyle et al. |
| 2003/0069597 A1 | 4/2003 | Petersen | 2004/0006364 A1 | 1/2004 | Ladd |
| 2003/0078519 A1 | 4/2003 | Salahieh et al. | 2004/0006365 A1 | 1/2004 | Brady et al. |
| 2003/0078614 A1 | 4/2003 | Satahieh et al. | 2004/0006366 A1 | 1/2004 | Huter et al. |
| 2003/0083692 A1 | 5/2003 | Vrba et al. | 2004/0006367 A1 | 1/2004 | Johnson et al. |
| 2003/0083693 A1 | 5/2003 | Daniel et al. | 2004/0006368 A1 | 1/2004 | Mazzocchi et al. |
| 2003/0100917 A1 | 5/2003 | Boyle et al. | 2004/0015184 A1 | 1/2004 | Boyle et al. |
| 2003/0100918 A1 | 5/2003 | Duane | 2004/0019363 A1 | 1/2004 | Hanson et al. |
| 2003/0100919 A1 | 5/2003 | Hopkins et al. | 2004/0034385 A1 | 2/2004 | Gilson et al. |
| 2003/0105484 A1 | 6/2003 | Boyle et al. | 2004/0039411 A1 | 2/2004 | Gilson et al. |
| 2003/0109824 A1 | 6/2003 | Anderson et al. | 2004/0044359 A1 | 3/2004 | Renati et al. |
| 2003/0114879 A1 | 6/2003 | Euteneuer et al. | 2004/0044360 A1 | 3/2004 | Lowe |
| 2003/0114880 A1 | 6/2003 | Hansen et al. | 2004/0049226 A1 | 3/2004 | Keegan et al. |
| 2003/0120303 A1 | 6/2003 | Boyle et al. | 2004/0059372 A1 | 3/2004 | Tsugita |
| 2003/0130680 A1 | 7/2003 | Russell | 2004/0059373 A1 | 3/2004 | Shapiro et al. |
| 2003/0130681 A1 | 7/2003 | Ungs | 2004/0082697 A1 | 4/2004 | Broome et al. |

| | | |
|---|---|---|
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102806 A1 | 5/2004 | Broome et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salahieh et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |
| 2004/0220611 A1 | 11/2004 | Ogle |
| 2004/0225321 A1 | 11/2004 | Krolik et al. |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Steeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015140 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |

| | | |
|---|---|---|
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0 472 334 A1 | 2/1992 |
| EP | 0533511 A1 | 3/1993 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |
| WO | WO 99/24104 A1 | 5/1999 |
| WO | WO99/44510 | 9/1999 |
| WO | WO00/67667 | 11/2000 |
| WO | WO01/10346 | 2/2001 |
| WO | WO01/45592 | 6/2001 |
| WO | WO01/87183 | 11/2001 |
| WO | WO 03/074118 A1 | 9/2003 |

* cited by examiner

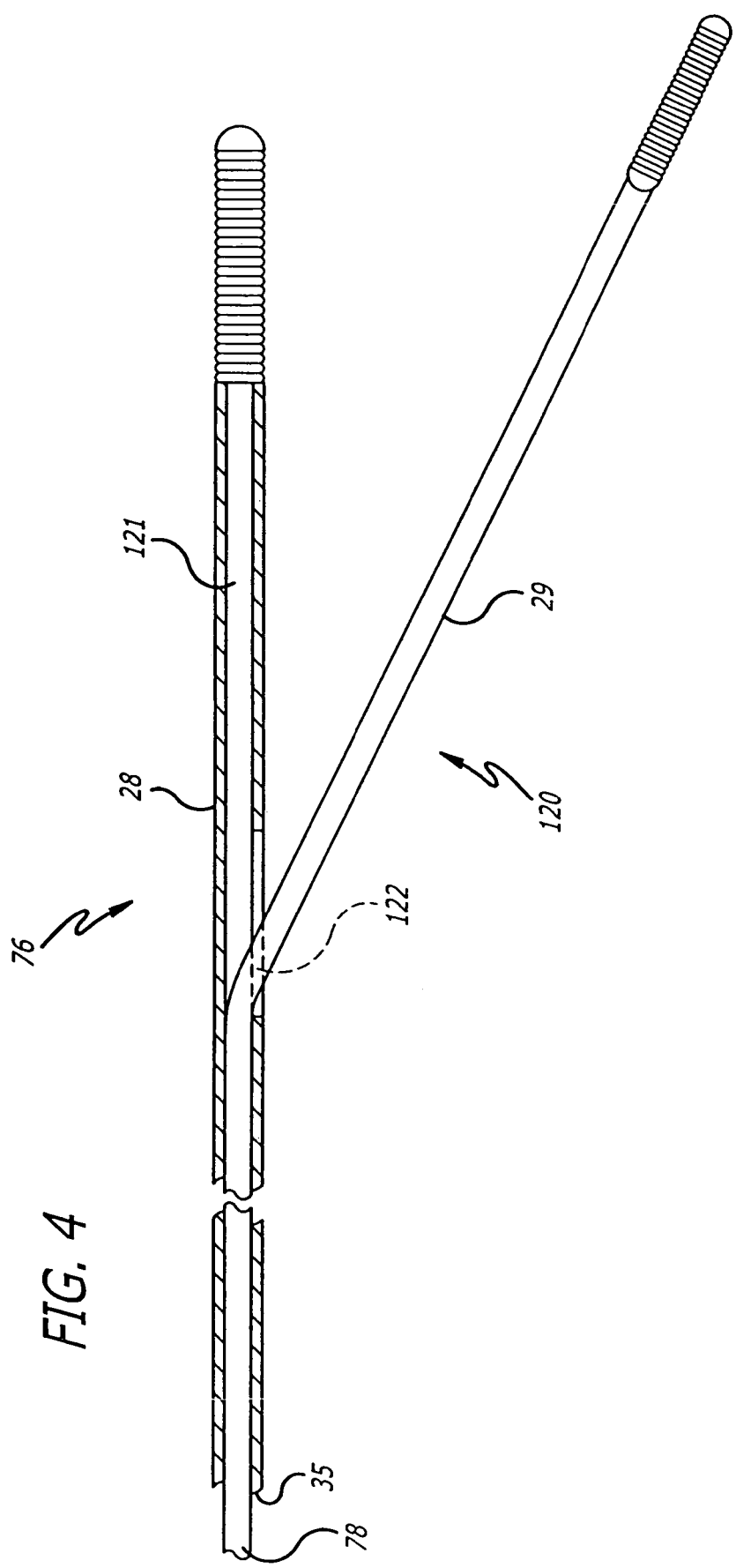

EMBOLIC FILTERING DEVICES FOR BIFURCATED VESSELS

BACKGROUND OF THE INVENTION

This application is a continuation of, and claims the benefit of the priority date of, prior application Ser. No. 10/180,287, filed Jun. 26, 2002 now U.S. Pat No 6,887,258.

The present invention relates generally to filtering devices used when an interventional procedure is being performed in a stenosed or occluded region of a biological vessel to capture embolic material that may be created and released into the vessel during the procedure. The present invention is more particularly directed to an embolic filtering device for use in a bifurcated vessel, such as, for example, a renal artery or carotid artery.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed biological vessel in which cutting blades are rotated to shave the deposited plaque from the arterial wall. A vacuum catheter distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the vacuum catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter, with the trapped embolic debris, can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the biological vessel.

Some prior art expandable filters are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When the treatment area is positioned proximate and upstream to a vessel bifurcation, it is sometimes necessary to place a single embolic filter in each of the branches of the bifurcated vessel. Utilizing a separate filter for each branch of the artery, however, can require the use of a larger delivery catheter and may occupy more space within the treatment site. As the filter for each branch of the vessel must be delivered and deployed individually, the use of multiple filters requires additional time to route and deploy the filters. Also, as the embolic filters are being removed from the branch vessels, captured embolic particles may be released from the filters and flow downstream through voids between the filters and the vessel wall. Also, if two separate guide wires are used, there may be a need for a special interventional device which has a large lumen in order to cross over both wires.

What has been needed is an expandable filter assembly for use in bifurcated vessels which can be deployed within, and retrieved from, each branch of the vessel simultaneously. An expandable filter also is needed which reduces the voids encountered between the individual filters and the vessel wall during retrieval of individual filters from the branches of a bifurcated vessel. The present invention satisfies these and other needs.

SUMMARY OF THE INVENTION

The present invention provides a bifurcated embolic protection device which is designed to remove emboli from bifurcated biological vessels. The present invention includes a bifurcated embolic filter having legs which may be dispersed into individual branches of a bifurcated vessel while minimizing voids between the filter and the bifurcated vessel. In this manner, the possibility of emboli floating downstream through either of the branch vessels is minimized.

In one aspect of the present invention, an embolic filtering device for use in a bifurcated biological vessel includes a delivery device having a first guide wire for directing the embolic filtering device to a first branch of the bifurcated vessel. The first guide wire has a proximal end and a distal end. The delivery device also has a second guide wire for directing the embolic filtering device to a second branch of the bifurcated vessel. This second guide wire also has a proximal end and a distal end. The second guide wire is coupled to the first guide wire and projects distally from a distal-end region of the first guide wire. The intersection between the first guide wire and the second guide wire forms a junction.

The embolic filtering device includes a filter support having a first deployment member and a second deployment member. In one aspect of the present invention, the first deployment member can be formed an expandable first loop and the second deployment member formed as an expandable second loop. Each of the first and second loops includes a first end, a second end and an apex positioned between the first end and the second end. The first and second ends of the first and second loops are coupled to the first guide wire at a position proximate to the junction between the first guide wire and the second guide wire and proximal to the junction. Each of the first and second loops includes a preset deflection proximate the first end and second end of the loop to permit the loop to diverge from a longitudinal axis of the first guide wire at the deflection of the loop.

The embolic filtering device further includes a filter element having an opening at a proximal end coupled to the filter support. The filter element includes a first leg which extends distally toward the distal end of the first guide wire from the first loop of the filter support. The first leg tapers toward a distal end of the first leg. The filter element includes a second leg which extends distally toward the distal end of the second guide wire from the second loop of the filter support. The second leg tapers toward a distal end of the second leg. The distal ends of the first leg and the second leg each include an aperture. The filter element further includes a crotch at a junction between the first leg and the second leg. With the filter element coupled to the filter support, the crotch of the filter element is positioned distal to the junction between the first guide wire and the second guide wire. The distal-end region of the first guide wire extends through the first leg of the filter element and through the aperture at the distal end of the first leg of the filter element while the second guide wire extends through the second leg of the filter element and through the aperture at the distal end of the second leg of the filter element.

In a detailed aspect of the invention, the distal end of the first guide wire and the distal end of the second guide wire each includes a coil tip. In another detailed aspect, the first guide wire and the second guide wire form a plane. A center of the first loop is positioned substantially on the plane between the first guide wire and the second guide wire on a side opposite from the second guide wire. A center of the second loop is positioned substantially on the plane between the first guide wire and the second guide wire, but on the same side as the second guide wire. In one particular embodiment of the present invention, the first loop and the second loop are positioned substantially longitudinally aligned along the first guide wire, while in another embodiment the first loop and the second loop are positioned longitudinally offset along the first guide wire. In a further aspect, the size of the perimeter of the first loop and the size of the perimeter of the second loop are nonequal. The opening at the proximal end of the filter element is coupled to the first loop and to the second loop. The opening of the filter element is coupled to a portion of the perimeter of the first loop of the filter support defined by a first position on the perimeter of the first loop and a second position on the perimeter of the first loop. Likewise, the opening of the filter element can be coupled to a portion of the perimeter of the second loop of the filter support defined by a first position on the perimeter of the second loop and a second position on the perimeter of the second loop. The first position on each of the first and second loops is located between the first end of the loop and the center of the loop, while the second position on each of the first and second loops is located between the second end of the loop and the center of the loop. In another detailed aspect of the first and second guide wires, the proximal end of the second guide wire is coupled to the first guide wire within the distal-end region of the first guide wire. In another detailed aspect of the first and second guide wires, the first guide wire further includes a hollow wire having a lumen throughout its length and an aperture within a wall of the wire positioned within the distal-end region of the first guide wire. In this aspect, the second guide wire is slidably coupled to the first guide wire and contained within the lumen of the first guide wire. The proximal end of the second guide wire extends beyond the proximal end of the first guide wire and the distal-end region of the second guide wire projects from the aperture of the first guide wire. In an additional detailed aspect of the invention, the length of the first leg of the filter element and the length of the second leg of the filtering element are nonequal.

In another aspect of the invention, an apparatus for filtering embolic material from a bifurcated biological vessel includes the embolic filtering device described above and a handle and a restraining sheath. The handle includes extending and retracting means. The restraining sheath includes a proximal end, a distal end and a lumen therebetween. The proximal end of the sheath is coupled to a distal end of the handle. The delivery device is contained within the lumen of the sheath and has a clearance fit with the sheath lumen. The filter support is extendible beyond the distal end of the sheath and retractable into the sheath by the means for extending and retracting the delivery device which correspondingly extends and retracts the filter support within the sheath. The first loop and the second loop are contracted and substantially parallel to the first guide wire upon retraction of the delivery device into the sheath, and the first loop and the second loop being expanded and project away from the first guide wire upon extension beyond the distal end of the sheath. The opening of the filter element is opened and closed when the first loop and second loop of the filter support are extended from and retracted into the sheath.

It is to be understood that the present invention is not limited by the embodiments described herein. The present invention can be used in arteries and other biological vessels. Other features and advantages of the present invention will become more apparent from the following detailed description of the invention, when taken in conjunction with the accompanying exemplary drawings.

BRIEF DESCRIPTION OF THE DRAWINGS

FIG. 4 is an elevational view, partially in cross section, of an alternative embodiment of the guide wires of the embolic filtering device.

DETAILED DESCRIPTION OF THE PREFERRED EMBODIMENTS

Figure 1:
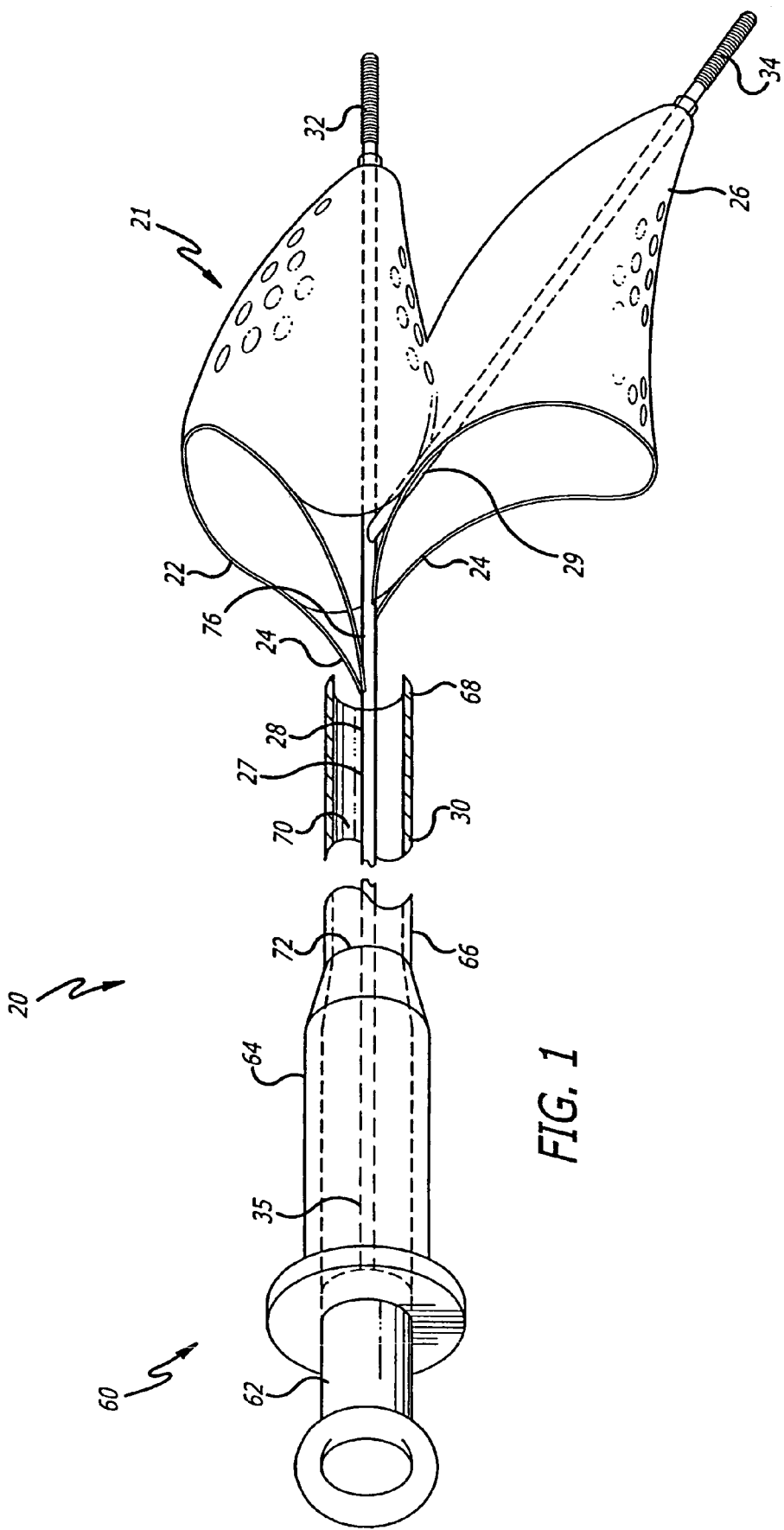
FIG. 1 is a perspective view of a particular embodiment of an apparatus for filtering emboli in a bifurcated biological vessel embodying features of the present invention.

Turning now to the drawings, in which like reference numerals represent like or corresponding elements in the drawings, FIG. 1 illustrates one particular embodiment of an apparatus 20 for filtering embolic material from a bifurcated vessel incorporating features of the present invention. The apparatus includes an embolic filtering device 21 designed to capture embolic debris which may be created and released into a bifurcated biological vessel during an interventional procedure. The embolic filtering device 21 includes an expandable bifurcated filter assembly 22 having a self-expanding filter support 24 and a bifurcated filter element 26 attached thereto. In this particular embodiment, the expandable filter assembly 22 is mounted onto the distal portion of a bifurcated delivery device 27 including a first elongated (solid or hollow) cylindrical shaft, such as a first guide wire 28, and a second elongated (solid or hollow) cylindrical shaft, such as a second guide wire 29. The first guide wire has a proximal end which extends outside the patient and is manipulated by the physician to deliver the filter assembly into the target area in the patient's vasculature. A restraining or delivery sheath 30 extends coaxially along the delivery device 27 in order to maintain the expandable filter assembly 22 in its collapsed position until it is ready to be deployed within the patient's vasculature. The expandable filter assembly may be deployed by the physician by simply extending the filter assembly 22 beyond the distal end of the restraining sheath 30. Alternatively, the expandable filter assembly is deployed by retracting the sheath proximally to expose the expandable filter assembly. Once the filter assembly is extended, the self-expanding filter support 24 immediately begins to expand within the biological vessel (see FIG. 3), causing the filter element 26 to expand as well.

The delivery device 27 extends through the filter support 24 and to the coil tips 32, 34 of the first 28 and second 29 guide wires. The full-length delivery device allows the physician to control the proximal end 35 of the first guide wire in order to steer the distal coil tips 32, 34 into the desired branches of the bifurcated vessel when delivering the embolic filtering device 21 through the patient's vasculature.

Figure 2:
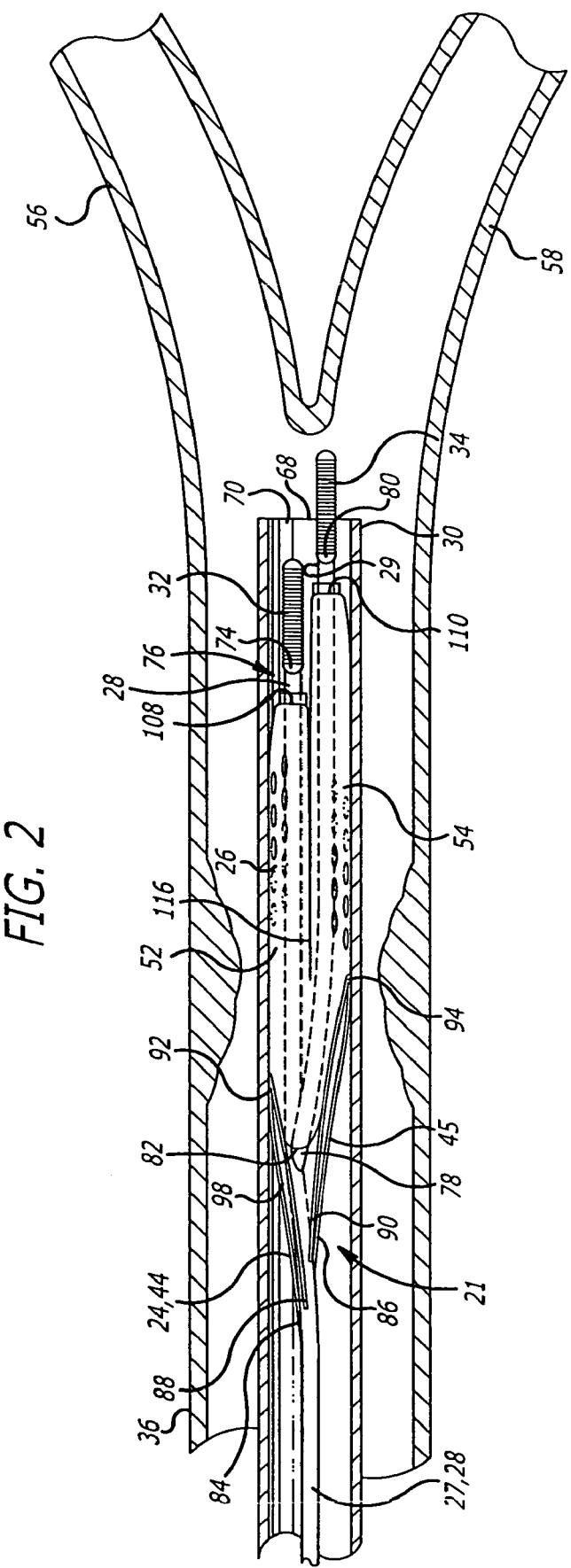
FIG. 2 is an elevational view, partially in cross section, of the apparatus for filtering emboli of FIG. 1 as it is being delivered to the location of a bifurcated biological vessel downstream from an area to be treated.
Figure 3:
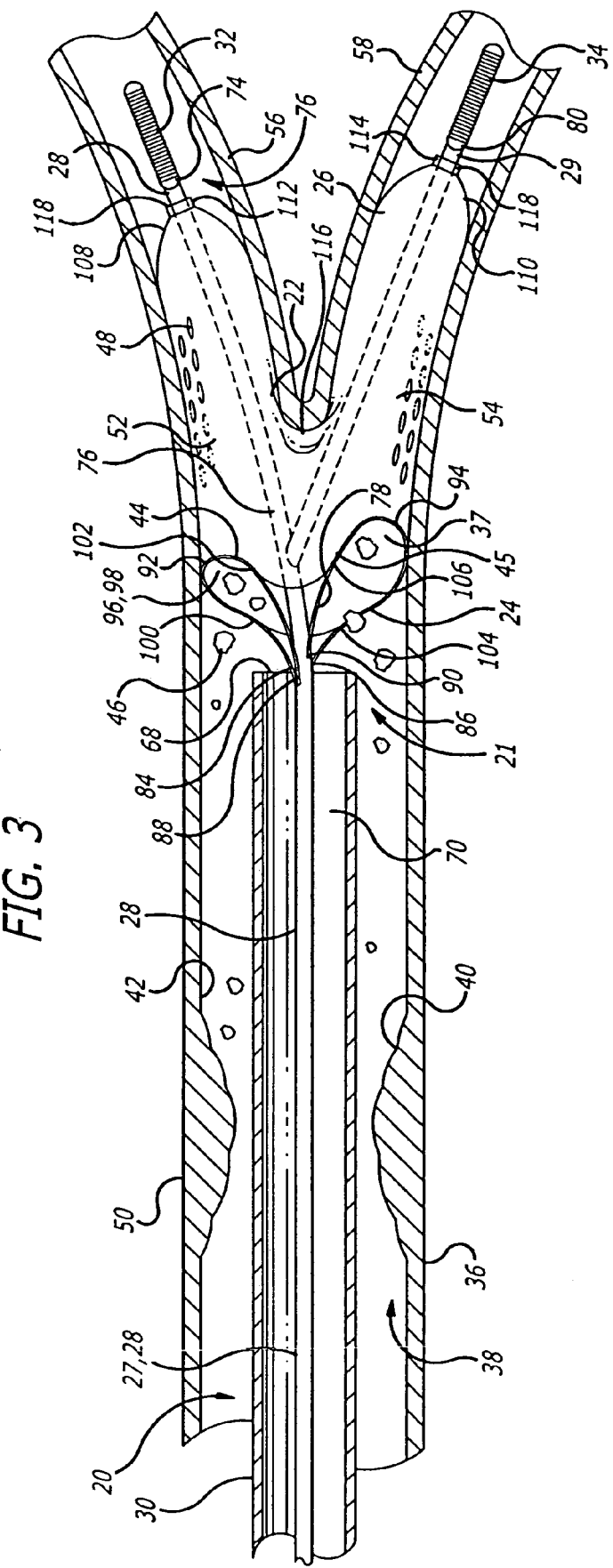
FIG. 3 is an elevational view, partially in cross section, similar to that shown in FIG. 2, wherein the embolic filtering device is deployed within the bifurcated biological vessel.

In FIGS. 2 and 3, the embolic filtering device 21 is shown as it is being delivered within an artery 36 or other biological vessel of the patient. More particularly, FIG. 3 shows the embolic filtering device 21 in its expanded position within the patient's artery 36. This portion of the artery 36 has a treatment site 38 in which atherosclerotic plaque 40 has built up against the inside wall 42 of an artery 36 of the patient. The filter assembly 22 is to be placed at the bifurcation 37 of the vessel which is distal to, and downstream from, the treatment site 38. For example, the therapeutic interventional procedure may include the implantation of a stent (not shown) to increase the diameter of an occluded artery and increase the flow of blood therethrough. It should be appreciated that the embodiments of the apparatus 20 described herein are illustrated and described by way of example only and not by way of limitation. Also, while the present invention is described in detail as applied to a bifurcated artery of the patient, those skilled in the art will appreciate that it can also be used in other bifurcated biological vessels. Additionally, the present invention can be utilized when a physician performs any one of a number of interventional procedures which generally require an embolic filtering device to capture embolic debris created during the procedure, such as balloon angioplasty, laser angioplasty or atherectomy.

The filter support 24 includes a first deployment member shown as a first loop 44 and a second deployment member shown as a second loop 45 which, upon release from the restraining sheath 30, expand the filter element 26 into its deployed position within the artery 36 (FIG. 3). While the deployment members are shown as self-expanding loops of wire in the present embodiment, those skilled in the art will appreciate that the deployment members can take on many shapes and sizes. Embolic particles 46 created during the interventional procedure and released into the bloodstream are captured within the deployed filter element 26. The filter element may include perfusion openings 48, or other suitable perfusion means, for allowing blood flow through the filter element 26. The filter element will capture embolic particles which are larger than the perfusion openings while allowing some blood to perfuse downstream to vital organs. Although not shown, a balloon angioplasty catheter can be initially introduced within the patient's vasculature in a conventional SELDINGER technique through a guiding catheter (not shown).

The delivery device 27 is disposed through the area of treatment and the dilatation catheter can be advanced over the first guide wire 28 within the artery 36 until the balloon portion is directly in the area of treatment 38. The balloon of the dilatation catheter can be expanded, expanding the plaque 40 against the wall 42 of the artery 36 to expand the artery and reduce the blockage in the vessel at the position of the plaque. After the dilatation catheter is removed from the patient's vasculature, a stent (not shown) could be implanted at the treatment site 38 using over-the-wire or rapid exchange techniques to help hold and maintain this portion of the artery 36 and help prevent restenosis from occurring in the area of treatment. The stent could be delivered to the treatment site on a stent delivery catheter (not shown) which is advanced from the proximal end of the first guide wire to the area of treatment.

The filtering device 21 is shown mounted to the distal portion of the delivery device 27 with the proximal portion of the bifurcated filter element 26 disposed in a branching portion of a trunk vessel 50 of a bifurcated biological vessel. First 52 and second 54 legs of the filter element are shown disposed within a first 56 and second 58 branch, respectively, of the bifurcated vessel. Any embolic debris 46 created during the interventional procedure will be released into the bloodstream and should enter the filter element 26. Once the procedure is completed, the interventional device may be removed from the patient, along with the filters. The filter assembly 22 can also be collapsed and removed from the artery 36, taking with it any embolic debris trapped within the filter element 26. A recovery sheath (not shown) can be delivered over the first guide wire 28 to collapse the filter assembly 22 for removal from the patient's vasculature.

Referring again to FIG. 1, the apparatus 20 for filtering embolic material from a bifurcated biological vessel may include a handle 60 which functions to manipulate the embolic filtering device 21. The handle may be of any type known in the art, such as pistol-like grip or syringe-type handles. FIG. 1 shows a syringe-type handle which includes a plunger 62 and a cylinder 64. The handle may include means for extending and retracting the delivery device 27 which is coupled to the handle. For instance, in the embodiment shown the delivery device may be extended and retracted by respectively pushing and drawing the plunger.

The elongate sheath 30 includes a first end 66 (proximal end), a second end 68 (distal end) and a lumen 70 therebetween. The proximal end 66 of the sheath may be coupled to a distal end 72 of the handle 60, such as at the cylinder 64, via means which are well known in the art, such as with an adhesive or by mechanical means. The lumen of the sheath is sized to contain the delivery device 27 and the filter assembly 22 with a clearance fit such that the delivery device and the filter assembly can be translated through the lumen by the extending and retracting means of the handle.

The materials which can be utilized for the restraining sheath 30 can be made from polymeric material such as cross-linked HDPE. The sheath can alternatively be made from a material such as polyolifin which has sufficient strength to hold the compressed filter support and has relatively low frictional characteristics to minimize any friction between the filtering assembly and the sheath. Friction can be further reduced by applying a coat of silicone lubricant, such as Microglide®, to the inside surface of the restraining sheath before the sheath is placed over the filtering assembly.

With further reference to FIGS. 2 and 3, the delivery device 27 is contained within the lumen 70 of the sheath 30. The delivery device includes the first guide wire 28 and the second guide wire 29. The first guide wire 28 may be used to direct the embolic filtering device 21 to the first branch 56 of the bifurcated vessel 36. As is specifically shown in FIG. 1, the first guide wire 28 includes a first end 35 (proximal end) and a second end 74 (distal end). The distal end of the first guide wire may include a coil shape 32 (coil tip) which facilitates in guiding the first guide wire through the vasculature and preventing injury to the vasculature. The proximal end 35 (FIG. 1) of the first guide wire may be coupled to the extending means of the handle 60, such as a distal end of the plunger 62 portion of the handle. A distal-end region 76 of the first guide wire may be extendible beyond the distal end 68 of the sheath 30 and retractable into the sheath by the means for extending and retracting the delivery device.

The second guide wire 29 may be used to direct the embolic filtering device 21 to the second branch 58 of the bifurcated vessel 36. The second guide wire 29 includes a first end 78 (proximal end) and a second end 80 (distal end). The distal end 80 of the second guide wire may include a coil shape 34 (coil tip) which facilitates in guiding the second guide wire through the vasculature and preventing injury to the vasculature. The second guide wire is coupled to the first guide wire 28 and projects distally from the distal-end region 76 of the first guide wire with the intersection between the first guide wire and the second guide wire forming a junction 82. A plane is also formed between the first guide wire and the second guide wire. Being coupled to the first guide wire, the second guide wire may be extendible beyond the distal end 68 of the sheath 30 and retractable into the sheath by the means for extending and retracting the delivery device 27. Upon retraction of the delivery device into the sheath, the second guide wire is forced to be substantially parallel to the first guide wire. The second guide wire projects away from the distal-end region of the first guide wire upon extension of the distal-end region of the first guide wire beyond the distal end 68 of the sheath.

With continued reference to FIGS. 2 and 3, the delivery device 27 may also include a filter support 24 having an expandable first loop 44 and an expandable second loop 45. The first 44 and second 45 loops may each be formed from a wire having a first end 84, 86 and a second end 88, 90. The dimensions of the first 44 and second 45 loops are determined in most cases by the size of the lumen of the vessel 36 in which embolic material 46 is sought to be filtered. The first and second ends of the first and second loops may be coupled to the first guide wire 28 through methods which are well known in the art, such as soldering or sandwiching the ends of the loops between the first guide wire and an annular sleeve (not shown). The first and second loops may be coupled to the first guide wire at a position proximate, or alternatively, distal to the junction 82 between the first guide wire and the second guide wire 29, proximal to the junction and proximate each other. The first and second loops each diverge from a longitudinal axis of the first guide wire. The first and second loops may each include a preset deflection proximate the first and second ends to facilitate the divergence of the first and second loops from the first guide wire. The first loop may be positioned such that a center of the first loop is located substantially on the plane between the first guide wire and the second guide wire on a side opposite the second guide wire. Similarly, the second loop may be positioned such that a center of the second loop is located substantially on the plane between the first guide wire and the second guide wire on the same side as the second guide wire.

The first 44 and second 45 loops may be extendible beyond the distal end 68 of the sheath 30 and retractable into the sheath by the means for extending and retracting the delivery device 27 which correspondingly extends and retracts the first and second loops. When the delivery device 27 is retracted within the sheath 30 (FIG. 2), the first loop 44 and the second loop 45 are mechanically stressed within their elastic limits to each form a long narrow loop, with the axis of each loop being substantially parallel to the longitudinal axis of the first guide wire 28 as shown in FIG. 2. While in this state, an apex 92 of the first loop 44 and an apex 94 of the second loop 45 each include a tight bend and consume large areas of a cross-section of the lumen 70 of the sheath.

If the apices 92, 94 of the first 44 and second 45 loops are positioned substantially longitudinally aligned with each other, it may cause difficulty in retracting the delivery device 27 into the sheath 30. To facilitate retraction of the delivery device 27 into the sheath, the first loop and the second loop may be positioned longitudinally offset along the first guide wire 28. For example, the second loop may be positioned either proximal or distal to the first loop along the first guide wire. By having the first and second loops positioned offset longitudinally, the apices of the first and second loops enter the sheath at different times and are longitudinally offset from each other when the first and second loops are contracted within the lumen of the sheath. Another means to longitudinally offset the apices of the first and second loops when the loops are contracted within the lumen of the sheath is to form the first and second loops in nonequal sizes. For example, the second loop may have either a larger or a smaller periphery than the first loop.

A suitable composition of nickel-titanium which can be used to manufacture the first loop 44 and the second loop 45 of the filter support 24 of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding filter support made in accordance with the present invention.

In one example, the first 44 and second 45 loops of the filter support of the present invention can be fabricated from a tube or solid wire of nickel-titanium (Nitinol) whose transformation temperature is below body temperature. After the loop is formed, the loop is heat treated to be stable at the desired final shape. The heat treatment also controls the transformation temperature of the filter support such that it is super elastic at body temperature. The transformation temperature is at or below body temperature so that the filter support is superelastic at body temperature. The filter support is usually implanted into the target vessel which is smaller than the perimeter of the filter support in the expanded position so that the loops of the filter support apply a force to the vessel wall to maintain the filter support in its expanded position. It should be appreciated that the filter support can be made from either superelastic, stress-induced martensite NiTi or shape-memory NiTi.

The embolic filtering device 21 may also include a filter element 26. The filter element may include an opening 96 at a first end 98 (proximal end) which is coupled to the filter support 24, such as to the first 44 and second 45 loops. The opening of the filter element may be coupled to a portion of the perimeter of the first loop defined by a first position 100 on the perimeter of the first loop and a second position 102 on the perimeter of the first loop. The first position on the first loop may be located between the first end 84 of the first loop and the center of the first loop. The second position on the first loop may be located between the second end 88 of the first loop and the center of the first loop. Likewise, the opening of the filter element may also be coupled to a portion of the perimeter of the second loop defined by a first position 104 on the perimeter of the second loop and a second position 106 on the perimeter of the second loop. The first position on the second loop may be located between the first end 86 of the second loop and the center of the second loop. The second position on the second loop may be located between the second end 90 of the second loop and the center of the second loop. As discussed earlier, the opening of the filter element may be opened and closed when the first loop and second loop of the filter support are extended from and retracted into the sheath 30.

The filter element 26 also includes at least a first leg 52 and a second leg 54 which extend distally from the opening 96 of the filter element. With the filter element coupled to the filter support 24, the first leg extends distally from the first loop 44 of the filter support and tapers toward a distal end 108 of the first leg. The second leg extends distally from the second loop 45 of the filter support and tapers toward a distal end 110 of the second leg. The distal ends 108, 110 of the first and second legs may each include an aperture 112, 114. The filter element further includes a crotch 116 positioned between the first leg and the second leg. With the filter element coupled to the filter support, the crotch is positioned distal to the junction 82 between the first guide wire 28 and the second guide wire 29. The distal-end region 76 of the first guide wire extends through the first leg 52 of the filter element and projects through the aperture 112 at the distal end of the first leg. The second guide wire 29 extends through the second leg 54 of the filter element and projects through the aperture 114 at the distal end of the second leg. To facilitate wear resistance between the filter element and the first and second guide wires, the apertures 112, 114 at the distal ends of the first and second legs of the filter element may each be lined with a sleeve 118 and the first and second guide wires may each extend through the respective sleeve. The ends of the sleeves can be made from a radiopaque material, such as gold or platinum, to increase visualization under fluoroscopy. The distal ends of the first and second legs of the filter element may be positioned longitudinally offset from each other to reduce the cross profile of the filter having captured embolic material therein to facilitate retraction of the embolic filter into the sheath.

In one embodiment of the present invention, the perimeter of the opening 96 of the filter element 26 is bonded to the first 44 and second 45 loops to secure the filter element to the filter support 24 through methods which are well known in the art, such as with adhesives, heat based bonding, or both. In an alternative embodiment (not shown), the filter element may be formed with a series of tab-like projections about the opening. The tab-like projections may be wrapped around the first and second loops of the filter support and bonded thereto through the methods described.

Polymeric materials which can be utilized to create the filtering element include, but are not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a pair of legs or similarly sized shapes utilizing blow-mold technology or dip technology. The perfusion openings 48 can be any different shape or size. A laser, a heated rod or other process can be utilized to create the perfusion openings in the filter material. The perfusion openings would, of course, be properly sized to catch the particular size of embolic debris of interest. Holes can be lazed in a spinal pattern or some similar pattern which will aid in the re-wrapping of the media during closure of the device. Additionally, the filter material can have a "set" put in it much like the "set" used in dilatation balloons to make the filter element re-wrap more easily when placed in the collapsed position.

Referring again to the delivery device 27, FIG. 1 depicts the first guide wire 28 as a solid wire. The second guide wire 29 is also depicted as a solid wire which is coupled to the distal-end region 76 of the first guide wire, such as by soldering. In this embodiment, the first and second guide wires are delivered to the first 56 and second 58 branches, respectively, of the bifurcated vessel 36 by advancing the distal end 68 of the sheath 30 to a position distal to the treatment site 38 and proximal to the vessel bifurcation 37. The delivery device may be partially extended, thereby partially extending the filter device 21, and rotated from the proximal end until the first and second guide wires are aligned with the first and second branches of the bifurcated vessel. The delivery device and first and second guide wires can then be further extended beyond the distal end of the sheath with the distal-end region 76 (FIG. 4) of the first guide wire 28 entering the first vessel branch and the distal-end region 120 of the second guide wire entering the second vessel branch. The first 52 and second 54 legs of the filter element 26 also enter the first and second vessel branches with the first and second guide wires, respectively. Further extension of the delivery device causes expansion of the filter support 24 within the trunk portion 50 of the vessel, thereby causing opening of the proximal end 98 of the filter element and completing deployment of the filter element.

In an alternative embodiment, FIG. 4 depicts the first guide wire 28 as a hollow tubular member which acts as a guide wire, such as a hypotube or polymeric tubing, having a lumen 121 throughout its length. The second guide wire 29 may include a solid or hollow wire which is slidably coupled to the first guide wire and contained within the lumen of the first guide wire. The proximal end 78 of the second guide wire 29 extends beyond the proximal end 35 of the first guide wire and the distal-end region 120 of the second guide wire projects from an aperture 122 within the wall of the distal-end region 76 of the first guide wire. Delivery of the first and second guide wires of this embodiment is similar to the method described above. However, the second guide wire may be translated proximally or distally from the proximal end to facilitate insertion of the distal-end region of the second guide wire and the second leg 54 of the filter element 26 into the second vessel branch 58.

The bifurcated filter of the present invention permits filtering of each of the branches of the bifurcated vessel and the branching portion of the trunk vessel with a single filter without any open voids between the filter and the vessel. As a result, the possibility of embolic material floating downstream through either of the branch vessels is minimized.

Further modifications and improvements may additionally be made to the device and method disclosed herein without departing from the scope of the present invention. Accordingly, it is not intended that the invention be limited, except as by the appended claims.

What is claimed is:

1. An embolic filtering device, comprising:
    a first guide wire having a proximal end and a distal end;
    a second guide wire having a proximal end and a distal end, the second guide wire being coupled to the first guide wire and projecting distally from a distal-end region of the first guide wire; and
    a bifurcated filter assembly having a first filter support and a second filter support, the bifurcated filter assembly being coupled to the first guide wire and including a single filter element attached to both the first and second filter supports, wherein the first and second filter support are positioned substantially longitudinally along the first guide wire.

2. An embolic filtering device, comprising:
    a first guide wire having a proximal end and a distal end;
    a second guide wire having a proximal end and a distal end, the second guide wire being coupled to the first guide wire and projecting distally from a distal-end region of the first guide wire; and
    a bifurcated filter assembly having a first filter support and a second filter support, the bifurcated filter assembly being coupled to the first guide wire and including a single filter element attached to both the first and second filter supports, wherein the first filter support is positioned longitudinally offset from the second filter support along the first guide wire.

3. An embolic filtering device, comprising:
    a first guide wire having a proximal end and a distal end;
    a second guide wire having a proximal end and a distal end, the second guide wire being coupled to the first guide wire and projecting distally from a distal-end region of the first guide wire; and
    a bifurcated filter assembly having a first filter support and a second filter support, the bifurcated filter assembly being coupled to the first guide wire and including a single filter element attached to both the first and second filter supports, wherein the filter element includes a first leg forming a storage area for capturing embolic material extending towards the distal end of the first guide wire and a second leg forming a second storage area for capturing embolic material extending distally towards the distal end of the second guide wire, and the first guide wire extends through the first leg and the second guide wire extends through the second leg.

4. An embolic filtering device, comprising:
    a first guide wire having a proximal end and a distal end;
    a second guide wire having a proximal end and a distal end, the second guide wire being coupled to the first guide wire and projecting distally from a distal-end region of the first guide wire; and
    a bifurcated filter assembly having a first filter support and a second filter support, the bifurcated filter assembly being coupled to the first guide wire and including a single filter element attached to both the first and second filter supports wherein each of the first filter support and the second filter support is a loop of wire which self-expands to a pre-determined configuration and the size of the perimeter of the loop of wires forming the first and second self-expanding filter supports is nonequal.

5. An embolic filtering device, comprising:
    a first guide wire made from a hollow tubular member having a lumen throughout its length and an aperture within a wall of the tubular member positioned within a distal-end region of the first guide wire;
    a second guide wire having a proximal end and a distal end, the second guide wire being slidable within the lumen of the first guide wire, the distal end of the second guide wire extending through the aperture in the first guide wire; and
    a bifurcated filter assembly having a first self-expanding filter support and a second self-expanding filter support, the bifurcated filter assembly being coupled to the first guide wire and including a single filter element attached to both the first and second self-expanding filter supports.

6. The embolic filtering device of claim 5, wherein:
    the filter element has an opening at a proximal end, the opening of the filter element being coupled to a portion of the first self-expanding filter support and to a portion of the second self-expanding filter support.

7. The embolic filtering device of claim 6, wherein the first guide wire extends through the first leg and the second guide wire extends through the second leg.

8. The embolic filtering device of claim 5, wherein:
    the filter element includes a first leg extending distally toward the distal end of the first guide wire and a second leg extending distally toward the distal end of the second guide wire.

9. The embolic filtering device of claim 8, wherein:
    the distal-end region of the first guide wire extends through the first leg of the filter element and the second guide wire extends through the second leg of the filter element.

10. The embolic filtering device of claim 5, wherein the first self-expanding filter is a loop of wire which self-expands to a pre-determined configuration.

11. The embolic filtering device of claim 10, wherein the second self-expanding filter is a loop of wire which self-expands to a pre-determined configuration.

12. The embolic filtering device of claim 11, wherein the loops of wire forming the first and second self-expanding filter supports are positioned substantially longitudinally along the first guide wire.

13. The embolic filtering device of claim 11, wherein the size of the perimeter of the loop of wires forming the first and second self-expanding filter supports are nonequal.

14. The embolic filtering device of claim 5, wherein the first self-expanding filter support is positioned longitudinally offset from the second self-expanding filter support.

* * * * *

UNITED STATES PATENT AND TRADEMARK OFFICE
CERTIFICATE OF CORRECTION

PATENT NO. : 7,572,272 B2  
APPLICATION NO. : 11/108309  
DATED : August 11, 2009  
INVENTOR(S) : Denison et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,572,272 B2  Page 1 of 1
APPLICATION NO. : 11/108309
DATED : August 11, 2009
INVENTOR(S) : Andy E. Denison et al.

It is certified that error appears in the above-identified patent and that said Letters Patent is hereby corrected as shown below:

Column 1, starting at line 41, insert -- is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to --

Signed and Sealed this

Fourteenth Day of December, 2010

David J. Kappos
*Director of the United States Patent and Trademark Office*